US00PP15303P2

(12) United States Plant Patent
Cooper

(10) Patent No.: US PP15,303 P2
(45) Date of Patent: Nov. 9, 2004

(54) SOUTH AMERICAN THORNLESS MESQUITE 'COOPER'

(50) Latin Name: *Prosopis Alba*
Varietal Denomination: Cooper

(76) Inventor: Karen B Cooper, 5055 N. Patterson Mesa Rd., Pima, AZ (US) 85543

( * ) Notice: Subject to any disclaimer, the term of this patent is extended or adjusted under 35 U.S.C. 154(b) by 3 days.

(21) Appl. No.: 10/660,280

(22) Filed: Sep. 10, 2003

(51) Int. Cl.[7] ..... A01H 5/00

(52) U.S. Cl. ..... Plt./226

(58) Field of Search ..... Plt./226

*Primary Examiner*—Anne Marie Grunberg
*Assistant Examiner*—Annette H Para
(74) *Attorney, Agent, or Firm*—Joseph H. Roediger; Gregory J. Nelson

(57) ABSTRACT

A new and distinct variety of South American Argentine ornamental mesquite which is particularly characterized by its rapid growth rate, total absence of thorns, large stature, distinctive foliage pattern and ability to thrive in a desert environment.

3 Drawing Sheets

The present invention relates to a new and distinct variety of South American Argentine ornamental mesquite known botanically as *Prosopis Alba*. The new variety will be name 'Cooper.' COOPER AMAZON is a Trade Mark applied to the variety to indicate the source of origin thereof.

BACKGROUND OF THE INVENTION

The new variety was discovered by me in 1987 from a field of 600 *Prosopis Alba* trees planted in grow bags in a field at our nursery in Mesa, Ariz. Five of the field were noted as being thornless and were potted into 15 gallon containers. During 1990, the five thornless *Prosopis Alba* were moved to our nursery (Cooper's Wholesale Nursery) in Pima, Ariz. and planted in a row running north and south, to the south of greenhouse #3. The designated *Prosopis Alba* mother tree #1 was planted at the north end of the row.

In 1992, at Cooper's Wholesale Nursery in Pima, Ariz., asexual reproduction of the new variety 'Cooper' began when I took 200 cuttings from *Prosopis Alba* mother tree #1, of which 6 rooted and grew. These 6 trees were planted in containers. Two years later in 1994, I took 100 cuttings from the best tree of the 6 trees that rooted and grew from the cuttings of 1992. From those cuttings, 5 rooted and grew. They were put in containers for further growth.

In 1997, I took 50 cuttings from the best tree of five trees that rooted and grew in 1994. From these cuttings, four trees grew. The source tree along with the four trees were placed in 20 gallon containers. All five trees were examined and found to exhibit the thornless characteristics of the *Prosopis Alba* mother tree #1.

From 1997 to 2000, the five *Prosopis Alba* clones grew and maintained the same characteristics of the *Prosopis Alba* mother #1. In 1999, seeds were gathered from the *Prosopis Alba* mother tree #1, planted and grown for root stock in preparation for budding using the five *Prosopis Alba* clones. In 2000, 250 root stock were budded using 50 buds from each of the five clones. The root stock was divided into five groups of 50 trees each. A 98 percent take in the buds was achieved.

The growth habit of the budded root stock was observed to be exceptionally vigorous, typically reaching a height of 10 cm in one week from the pop of the bud. After two weeks, an average of 20 to 25 cm of growth was recorded. This rapid growth habit continues until a height of about 102 cm is reached at which time branching begins to occur. The diameter of the trunk of the budded root stock trees was observed to increase at approximately the same rate as the increase in height. As a result, none of the young *Prosopis Alba* 'Cooper' mesquite trees required staking. All of the 245 trees exhibited the same characteristics as the mother tree #1, including the lack of thorns.

In 2001, 500 trees were budded using the five *Prosopis Alba* clones plus one tree from each of the five groups of budded root stock. The growth habit for the 500 trees was the same as that exhibited by the group of 245 trees grown in year 2000. All of the aforementioned asexual propagation activity occurred at our nursery in Pima, Ariz. Due to the rapid growth of the young trees, none of the *Prosopis Alba* 'Cooper' mesquite required staking. All of the trees were thornless. This characteristic is in marked contrast to the common *Prosopis Alba* which has thorns up to 8 cm in length.

SUMMARY OF THE NEW VARIETY

The tree of this new variety is unusual for the species in that it possess a rapid growth rate and matures to larger stature tree than any known thornless *Prosopis Alba* Argentine mesquite. Further, this new variety is thornless with no occurrences of thorns taking place over a period of sixteen years encompassing multiple generations of the *Prosopis Alba* 'Cooper' mesquite.

The mature tree reaches a height of about 25 feet with a canopy of 40 feet and a trunk diameter of about 45 inches. Lack of water did not effect its growth habit. The new variety is characterized by large and numerous leaves. Thus, the new variety provides an excellent shade source with minimal care for the desert environment.

The total absence of thorns further enhances the attractiveness of this tree for use in populated areas.

The new variety is hardy having experienced lengthy and hard freezes. Weather patterns having high winds including a tornado resulted only in a stripping of the leaves. No damage to the branches or trunk was noted. The *Prosopis Alba* 'Cooper' has demonstrated exceptional strength in a wide range of adverse weather conditions.

DESCRIPTION OF THE NEW VARIETY

Figure 1:
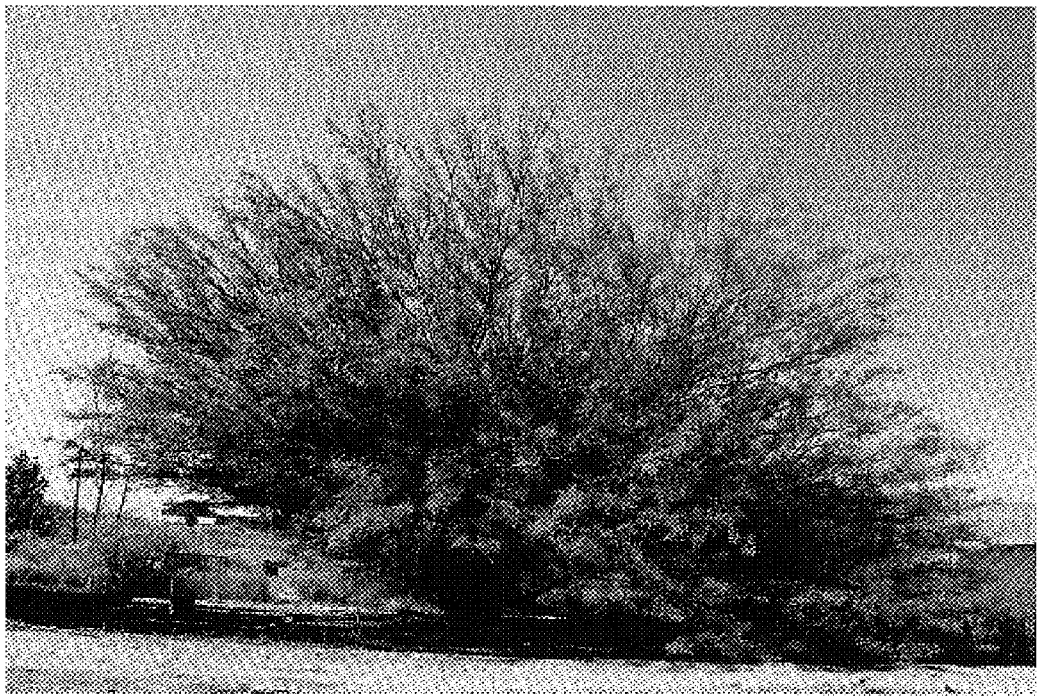
FIG. 1 is a color photograph of the 13 year old parent tree of the new variety.
Figure 2:
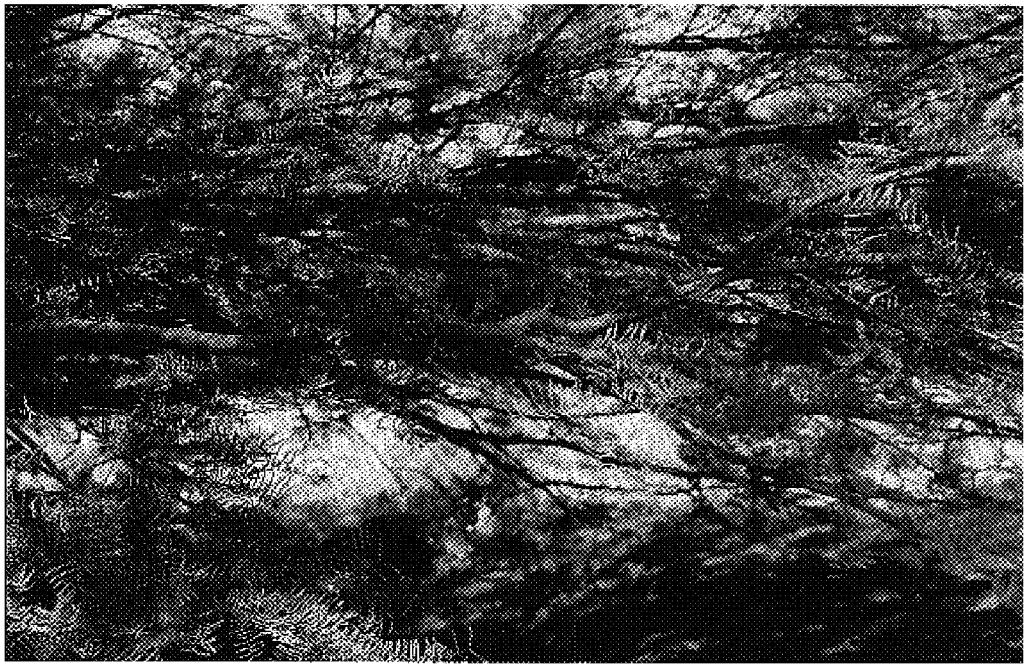
FIG. 2 is a color photograph showing the branching of the new variety of tree.
Figure 3:
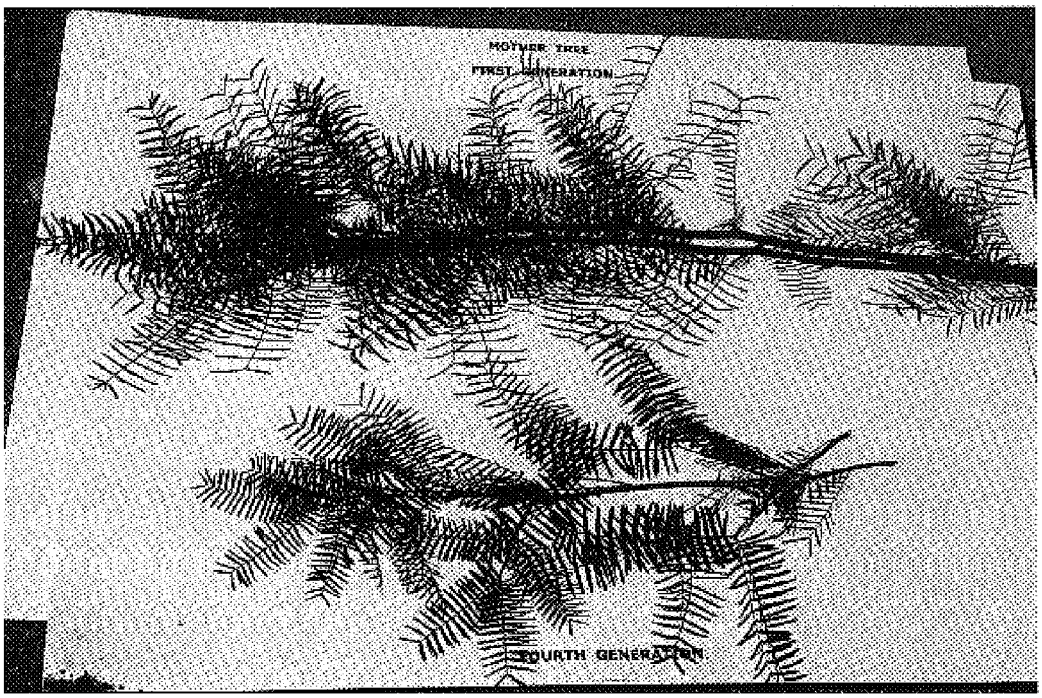
FIG. 3 is a color photograph showing the distinctive pattern of the foliage of the parent tree and that of a fourth generation tree.
Figure 4:
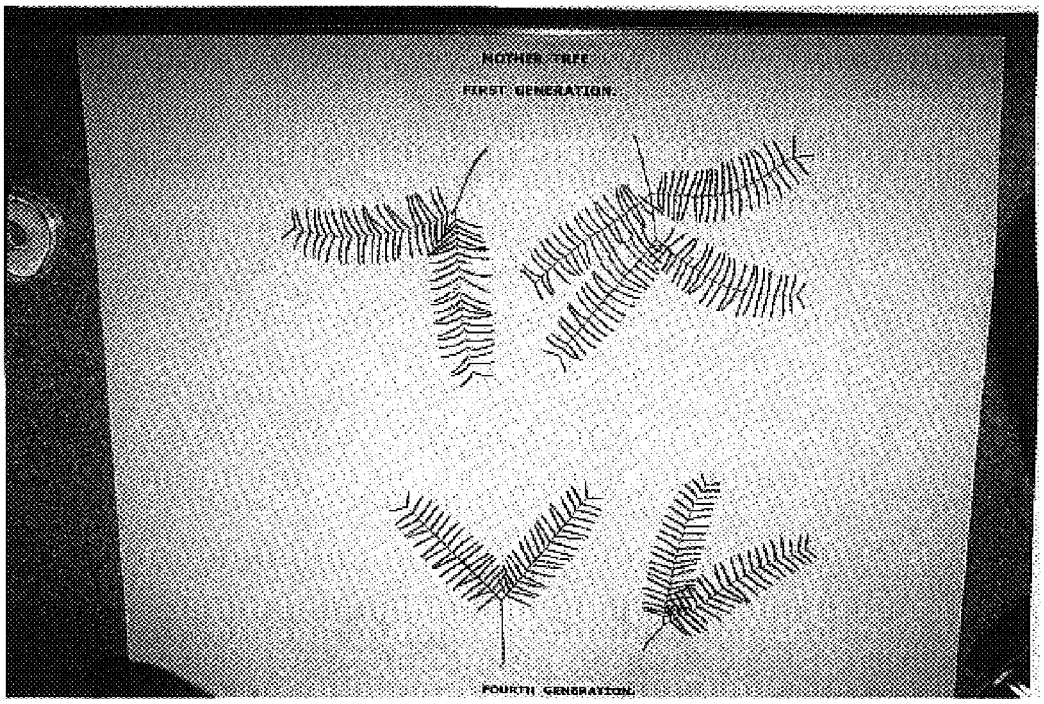
FIG. 4 is a color photograph displaying the structure of the leaves.
Figure 5:
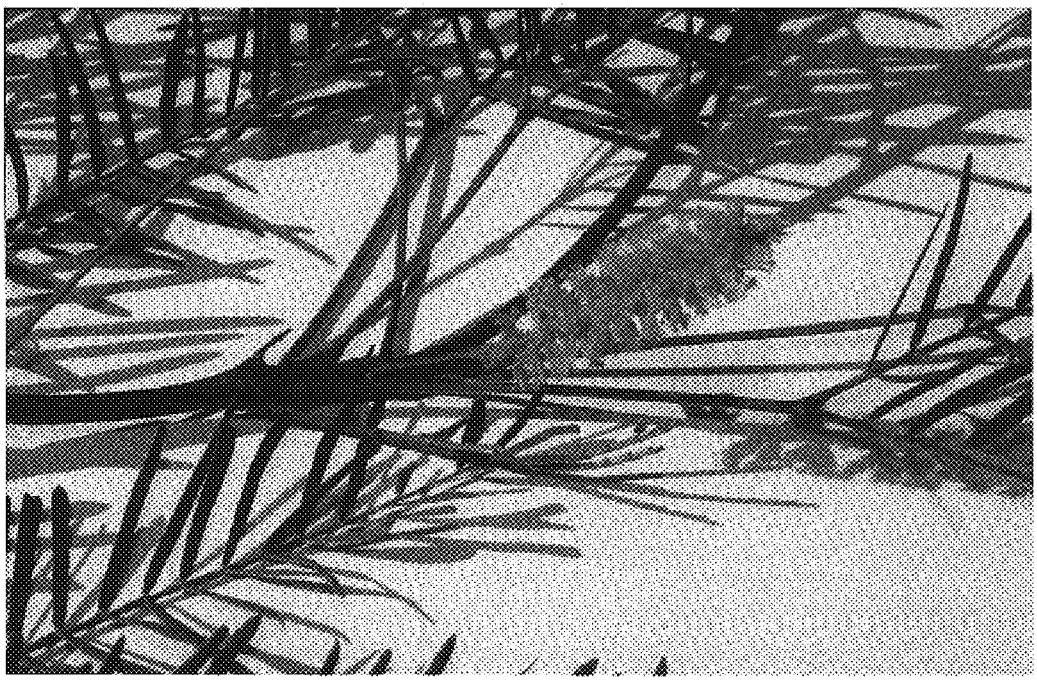
FIG. 5 is a color photograph showing the bloom of the new variety.

The following is a detailed description of my new variety of *Prosopis Alba* named 'Cooper'. All color designations herein are made in accordance with The Royal Horticultural Society Colour Chart.

Tree: At maturity, the tree height is about 8 m with a canopy of 13 m and a trunk diameter of 1.14 m. The *Prosopis Alba* 'Cooper' mother tree #1 is 15 years old and received drip irrigation for the first three years. Thereafter no irrigation was provided. The lack of water did not alter its growth rate of about 1 m per year.

The diameter of the main trunk measures approximately 114 cm, with the main crotch exhibiting a 30 degree departure from vertical. The primary or lower branches (approximately 7 cm or larger in diameter) which eminate from the main crotch depart therefrom at between 10 degrees and 30 degrees from vertical. Branches secondary, tertiary and beyond depart from vertical consistently with the primary branches. Overall branching from the tree bottom to the tree top appears to be symmetrical and creates a full and robust canopy.

The trunk color of the mature *Prosopis Alba* 'Cooper' mesquite is gray group 201-A (R.H.C.) and measures approximately 114 cm in diameter. The bark has a rough texture, but not loose and shaggy. Branches of 5 cm to 7 cm in diameter are also color gray group 201-A (R.H.C.) and maintain a rough texture while the terminal branches 3 cm or less in diameter become smooth with a polished look and are the color of group grayed-orange 175-A (RHC).

Bark: The bark on the trunk of the mature *Prosopis Alba* 'Cooper' is rough, but not shaggy. The young terminal branches are smooth with a polished look. At about 66 cm from the ground, the fissures on the trunk measure 7 mm wide. At 159 cm, the trunk fissures are 3 mm wide and disappear beyond that height.

The bark color is gray group 201-A for the trunk and branches of at least 5 cm in diameter. The color of smaller diameter terminal branches is greyed-orange group 175-A.

Thorns: The *Prosopis Alba* 'Cooper' has been found to be completely thornless from the mother tree #1 through three generations of asexual reproduction by cuttings followed by cloning via budding from the third generation. No thorns appeared at any stage of growth, nor did any develop into maturity.

Foliage: All generations of the new variety exhibit the same foliage pattern with an average of five petioles coming from the node of the branch, with one pair of pinnae per each petiole. The petioles are 4 to 4.5 cm long and the individual pinnae is 13–15 cm long.

Each pinnae has an average of 18 pairs of leaflets with a spacing of about 1.5 cm therebetween. Each leaflet is about 2.75 cm long and 2 mm wide.

The terminal branches have about 43 pairs of leafs in a distance of 55 cm, with an average of 5 to 5.5 cm between the internodes. The color of the leaves is group yellow-green 147-B.

Flowering: The bloom of the new variety is typically 6.5 to 7.5 cm in length and 1.25 cm wide. The color of the bloom is group yellow-orange 21-C.

The appendages on which the bud forms are on average 6 cm to 9 cm long and 0.15 cm in diameter with the color group yellow-green 147-D. Buds grow in a spiraling pattern around the pedicel and number approximately from 110 to 160 with an oval shape. When buds are mature they measure about 0.31 cm in length with the color group green 139-C (RHC). When buds open the calyx contains approximately 5 points, measuring about ¼ cm from base to tip, giving it a star shape and maintaining the color group 139-C. An average of 10 stamen surround the stigma inside the calyx, measuring about 0.62 cm in length with the color group yellow-orange 21-C. I have observed, on an average, that one seed pod per bloom is formed. Most of the pollination of the new variety is dependent on bees and the weather.

The flower is comprised of the 110 to 160 buds. When all buds are open and in full bloom, the flower measures approximately 6½–7½ cm in length and 1¼ cm in width showing the color group yellow-orange 21-C (R.H.C.).

The seed pods average 13–16 cm long, 2 cm wide and 2 mm thick. Mature seed pods that have fallen from the tree have a curved shape and color of group greyed-yellow 161-B. The number of seed per pod is 18 to 24. The seeds are 8 mm long and 5 mm wide with a color of group greyed-orange 164 B.

Disease Resistant: In 1990, the mother tree #1 and the four other thornless mesquites were planted in soil where cotton had been grown and which contained cotton root rot (*Phymatotrichum Omnivorum*). The trees were unaffected by the root rot in the soil. No stem cankers have ever been observed on the mother tree #1 or any of the clone trees.

Cold Hardiness: After experiencing an extremely hard freeze of a 16° F. low and a 36° F. high for five consecutive days, the mother tree #1 sustained no trunk damage and retained 50 percent of the leaves. Similar weather patterns of freezing occurred during the period of 1992 through 1999 with no damage to the branches or trunk on the trees of this new variety.

In July of 2003, a hail storm with winds of 60 mph for a period of one hour took place and over 400 trees of this new variety were exposed. No apparent damage was sustained. The height of the trees in containers at that time was 102 to 122 cm. The strength of the *Prosopis Alba* 'Cooper' variety under severe weather considerations is notable.

I claim:

1. A new and distinct variety of *Prosopis Alba* tree named 'Cooper', substantially as illustrated and described, characterized by a complete lack of thorns, rapid growth in girth and height, exceptional strength, ability to withstand severe weather conditions including wind, hail and freezing temperatures with no apparent damage, a resistance to stem canker and root rot, and its distinctive foliage as described herein.

* * * * *